(12) United States Patent
Simpson et al.

(10) Patent No.: US 7,361,164 B2
(45) Date of Patent: Apr. 22, 2008

(54) MULTI-OUTLET MEDICAL DISPENSING DEVICE

(75) Inventors: Philip J. Simpson, Escondido, CA (US); David G. Matsuura, Encinitas, CA (US); Walter D. Gillespie, San Diego, CA (US); James A. Trinchera, Leucadia, CA (US); Mark P. Costa, Milton (CA); Taras Worona, Etobicoke (CA); Hao Chen, Mississauga (CA); David A. R. Kanbergs, Milton (CA); Kathleen Chancellor-Maddison, Mississauga (CA); Roy Zhao, Brampton (CA); Bernard C. B. Lim, Oakville (CA)

(73) Assignee: Vasogen Ireland Limited (IE)

( * ) Notice: Subject to any disclaimer, the term of this patent is extended or adjusted under 35 U.S.C. 154(b) by 229 days.

(21) Appl. No.: 11/119,062

(22) Filed: Apr. 28, 2005

(65) Prior Publication Data

US 2005/0245872 A1    Nov. 3, 2005

Related U.S. Application Data

(60) Provisional application No. 60/565,855, filed on Apr. 28, 2004.

(51) Int. Cl.
*A61M 5/315* (2006.01)

(52) U.S. Cl. .............. 604/236; 604/122; 604/187; 604/218

(58) Field of Classification Search ........... 604/122, 604/124, 125, 126, 181, 187, 190, 21, 236, 604/123, 127, 218, 237, 537, 538, 539
See application file for complete search history.

(56) References Cited

U.S. PATENT DOCUMENTS

| | | | | |
|---|---|---|---|---|
| 4,772,273 A | * | 9/1988 | Alchas | 604/218 |
| 5,971,953 A | * | 10/1999 | Bachynsky | 604/90 |
| 2005/0043684 A1 | * | 2/2005 | Basta et al. | 604/164.13 |

* cited by examiner

*Primary Examiner*—Kevin C. Sirmons
*Assistant Examiner*—Laura C. Schell
(74) *Attorney, Agent, or Firm*—Foley & Lardner LLP

(57) ABSTRACT

A medical delivery device comprising an elongate body having a plunger slidably and sealingly engaged to form a cavity to receive fluid materials and a first outlet disposed at an end of said body and has a male luer end portion and a valve assembly is disposed within the first outlet. The valve assembly has a valve means movable between an open position and a closed position and biasing means for biasing the valve means to a closed position. Actuating means are disposed within the male luer end portion and coupled to the valve means such that the valve means is movable to an open position when a female luer end portion of a medical accessory is coupled with the male luer end portion. A second outlet is disposed at the same end as the first outlet for controlling the exchange of gases from the environment to said cavity under the action of the plunger. Lastly, a third outlet is disposed at the same end as the first outlet for controlling the exchange of gases from the cavity to the environment under the action of the plunger.

35 Claims, 5 Drawing Sheets

MULTI-OUTLET MEDICAL DISPENSING DEVICE

TECHNICAL FIELD

The present invention relates to medical dispensing devices for dispensing medical or biological liquids by injection or other forms such as, for example, syringes and catheters.

BACKGROUND ART

A major concern of health professionals is the safe handling of biological materials and medicines. Syringes are commonly used medical dispensing devices but there are risks to both the health professional and the patient in using these common devices. Although there have been a number of developments over the years, significant risks still remain.

When syringes are filled with biological fluids or medicines, it is usually necessary to remove any gaseous materials remaining in the body of the syringe prior to injection into the patient. The reason for this is that it is potentially fatal to inject a patient with air or gas since the gas bubble will form an embolism in the patient with likely serious, and possibly fatal, consequences.

The usual procedure for purging gas from a syringe is for the health professional to hold the syringe upright and to tap the body of the syringe to send all gas bubbles to the top of the syringe. The plunger is then actuated to push the gas out of the syringe. A piece of cotton gauze is placed at the end of the syringe (usually with a needle) and the gas is expelled along with some of the liquid to ensure that all gas has been expelled from the system. If a needle is placed at the end of the syringe and the action of the plunger is not controlled well, it is possible that the liquid can be expelled for a considerable distance. As can be seen, there is some loss of the medicine or biological fluid, with obvious risks for contaminating others with the material in the syringe.

In addition, there are certain circumstances where it would be advantageous to allow air into the syringe in a controlled manner. At present, one must actuate the plunger and thus allow a large amount of air into the syringe.

Additionally, it is advantageous to have a medical dispensing device with a valve at the first outlet which must be actuated to allow flow of liquid into or out of the syringe.

At present there are medical dispensing devices which have one way valves, purging valves, and air inlet valves. However, it would be advantageous to encompass all three functions integrally in one medical dispensing device. The present invention provides a medical dispensing device which incorporates all three functions, or combinations of the three functions, in one device.

SUMMARY OF THE INVENTION

Briefly described, the invention provides, from one aspect, a medical delivery device comprising an elongate body having a plunger slidably and sealingly engaged to form a cavity to receive fluid materials. A first outlet is disposed at an end of said body, and has a male luer end portion and a valve assembly disposed within the first outlet. The valve assembly has a valve means movable between an open position and a closed position and biasing means for biasing the valve means to a closed position. Actuating means are disposed within the male luer end portion and coupled to the valve means such that the valve means is movable to an open position when a female luer end portion of a medical accessory is coupled with the male luer end portion. A second outlet is disposed at the same end as the first outlet for controlling the exchange of gases from the cavity to the environment under the action of the plunger. A third outlet is disposed at the same end as the first outlet for controlling the exchange of gases from the environment to the cavity under the action of the plunger. In any of the embodiments of the invention, the communication between the outlets and the cavity can be separate, common between the outlets, or common between combinations of the outlets.

In an embodiment of the invention, a one-way valve is disposed within a housing in the second outlet for exchange of gaseous materials from the cavity of the elongate body to the environment. Preferably, the one-way valve disposed within the housing is a duckbill valve. In a preferred form of the invention, a hydrophobic membrane is disposed between the one-way valve and the cavity of the elongate body to prevent liquid from traveling from the cavity to the one-way valve. The hydrophobic membrane may be integral with the one-way valve, and disposed proximal to the cavity of the elongate body.

In a preferred embodiment of this aspect of the invention, the aforementioned third outlet for exchange of gaseous materials from the environment to the cavity suitably includes a housing in which is disposed a one-way valve. Preferably, the one-way valve is an umbrella valve. A filter is preferably disposed between the one-way valve and the environment to prevent entry of bacteria, viruses, or other materials which would compromise the sterility of the contents of the medical dispensing device. The filter may be disposed between the one-way valve and the cavity of the elongate body and suitably has the additional property of being hydrophobic to prevent liquid from traveling from the cavity to the one-way valve. Preferably, a filter and a hydrophobic membrane are separately disposed in series, between the one-way valve and the cavity of the elongate body, with the hydrophobic membrane facing the cavity. The filter is suitably disposed between the environment and the one-way valve and the hydrophobic membrane is disposed between the one-way valve and the cavity.

In a further embodiment of the invention, the valve assembly is comprised of an actuating member having upstanding arms, a resilient member having resilient cam arms, a valve stem, valve head and valve seat. The valve assembly is mounted on a housing having a central bore coaxial with central apertures on the actuating and resilient members and having fluid communication with the cavity. The housing has slots for locating the resilient cam arms. The valve stem, valve head, and valve seat are disposed in a tubular housing which is itself part of an end housing. Upon rearward movement of the actuating member, the cam arms flex outwards, thus allowing the valve head to be taken off the valve seat, permitting fluid communication with the cavity. The resilient cam arms bias the valve head against the valve seat in the absence of force causing rearward movement of the actuating member.

Suitably, the end housing has a male luer portion having complementary fit with a female luer portion of a medical accessory. When a medical accessory with a female luer portion, such as a needle, is inserted onto the male luer portion, the bottom surface of the needle abuts against the top surface of the actuating member arms to cause rearward movement of the actuating members and consequently the resilient member and the valve head are moved rearwardly as well. There is thus fluid communication through the tubular member, valve stem, and to the cavity.

In yet another embodiment, the invention provides a medical dispensing device comprising an elongate body having a plunger slidably and sealingly engaged therein to form a cavity to receive fluid materials. A first outlet is disposed at an end of said body and comprises a male luer end portion. There is a valve assembly disposed within the first outlet having a valve means movable between an open position and a closed position, and biasing means for biasing the valve means to a closed position. Actuating means are disposed within the male luer end portion and are coupled to the valve means such that the valve means is movable to an open position when a female luer end portion of a medical accessory is coupled with the male luer end portion. A second outlet is disposed at the end for controlling the transfer of gases between the environment and the cavity under the action of the plunger. The second outlet in this embodiment may similarly have a housing containing a one-way (e.g. duckbill) valve and a hydrophobic membrane as described above.

There may also be a one-way valve disposed within a housing in the second outlet for exchange of gaseous materials from the environment to the cavity such as an umbrella valve, optionally with a filter is disposed between the one-way valve and the environment to prevent entry of bacteria, viruses, etc., as described above.

There may also be a two-way valve disposed within a housing in the second outlet for exchange of gaseous materials between the environment and the cavity. Preferably, the two-way valve is a combination valve having a duckbill valve portion and umbrella valve portion with the umbrella valve portion being proximal to the cavity and having an integral membrane having hydrophobic properties and filter properties to prevent entry of bacteria, viruses, or other materials which would compromise the sterility of the contents of the medical dispensing device. In yet another aspect, a filter is disposed distal to the duckbill valve portion to prevent entry of bacteria, viruses, or other materials which would compromise the sterility of the contents of the medical dispensing device, and a hydrophobic membrane is disposed between the umbrella valve portion and the cavity to prevent liquid from traveling from the cavity to the two-way valve. In a further aspect, the filter and the hydrophobic membrane are disposed in series between the umbrella valve portion and the cavity, with the hydrophobic membrane being proximal to the cavity. Hydrophobic membrane is disposed between the one-way valve and the cavity.

In another embodiment, the invention comprises a medical dispensing device having a body, a cavity within the body, a first outlet disposed at an end of the body, and at least one secondary outlet at the said end of the body for controlling the exchange of gases between the cavity and the environment, as well as transferring liquid from the cavity out through the first outlet. A pressure exerting means for exerting pressure or decreasing on or within the body is associated with the medical dispensing device, such that the exchange of gases between the cavity and the environment is achieved or the transferal of liquid from the cavity through the first outlet. The pressure exerting means may be a plunger, a peristaltic pump, or similar device, or hydrostatic pressure.

As noted, the present invention can present itself as several embodiments. Each embodiment may have a combination of the individual parts and features described herein, such as valves, membranes, filters, outlets and housings, assembled into a working arrangement. The description below, and illustrations, are of specific preferred but non-limiting embodiments.

DESCRIPTION OF THE BEST MODE

Figure 1:
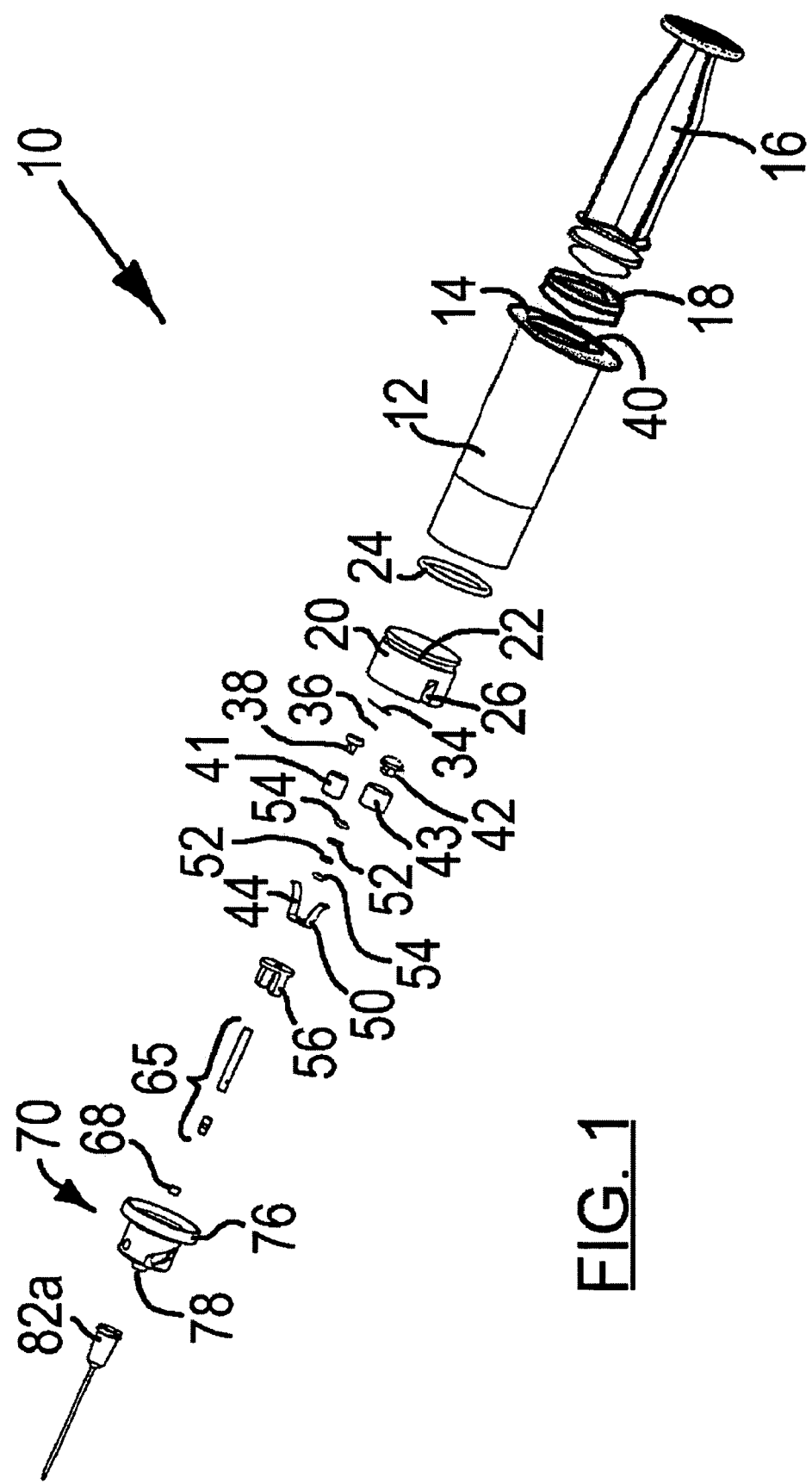
FIG. 1 is an exploded view of a medical dispensing device according to the preferred embodiment of the invention.

FIG. 1 shows generally, in exploded view, the medical dispensing device of the preferred embodiment of the present invention. Syringe 10 has an elongate, cylindrical, hollow body 12 having outwardly extending flanges 14 at one end as finger grips. Plunger 16 has an elastomeric head 18 attached at one end of plunger 16. Elastomeric head 18 provides sliding and sealing engagement with the inner surface of body 12. A cylindrical housing 20 having a circumferential groove 22 for placement of O-ring 24 for watertight sealing is placed in the front end of body 12. Housing 20 has inwardly and upwardly extending slots 26, a central bore 28 (as seen in FIG. 2), and bores 30 and 32 adjacent to central bore 28.

A hydrophobic membrane 34 is located in a slot 35 (see FIG. 3) on the side of housing 20 facing cavity 40 and is associated with washer 36 and a duckbill valve 38 to provide one-way flow of gaseous material from the cavity 40 of body 12, by way of a passageway 39, through duckbill valve 38 to the environment through a central outlet opening 41a. Hydrophobic membrane 34 prevents liquid from cavity 40 entering duckbill valve 38 but allows gas to pass through, thus allowing purging of gas from cavity 40 to the environment through central outlet opening 41a without release of liquid. Duckbill valve 38 is disposed within a duckbill valve housing 41, having central outlet opening 41a, which is itself disposed within bore 30, thus permitting release of gaseous material to the environment though end housing 70. In instances where gaseous material has to be purged from cavity 40 and liquid materials are also present, plunger 16 can be pushed to force gaseous material through hydrophobic membrane 34 and consequently through duckbill valve 38, without liquid materials being expelled to the environment.

An umbrella valve 42 is disposed within an umbrella valve housing 43 (see FIG. 5) and umbrella valve housing has a central opening 45, where the umbrella valve housing 43 is located in bore 32 to permit one-way flow of gaseous material from the environment to cavity 40. A membrane (not shown) having hydrophobic and filter properties to prevent entry of bacteria, viruses, or other materials which would compromise the sterility of the contents of the medical dispensing device is placed in a slot on the side of housing 20 facing cavity 40 similar to slot 35 to prevent liquid from cavity 40 from entering bore 32 or alternatively disposed in a slot on the exterior side of umbrella valve 42. Gaseous material can travel from the environment through end housing 70, to umbrella valve 42 and through passageway 47 to cavity 40 under action of plunger 16. Umbrella valve 42 may also be set to a predetermined crack-open pressure to allow fluid such as blood to be drawn into the cavity 40 under action of the plunger if desired, through umbrella valve 42.

Figure 2:
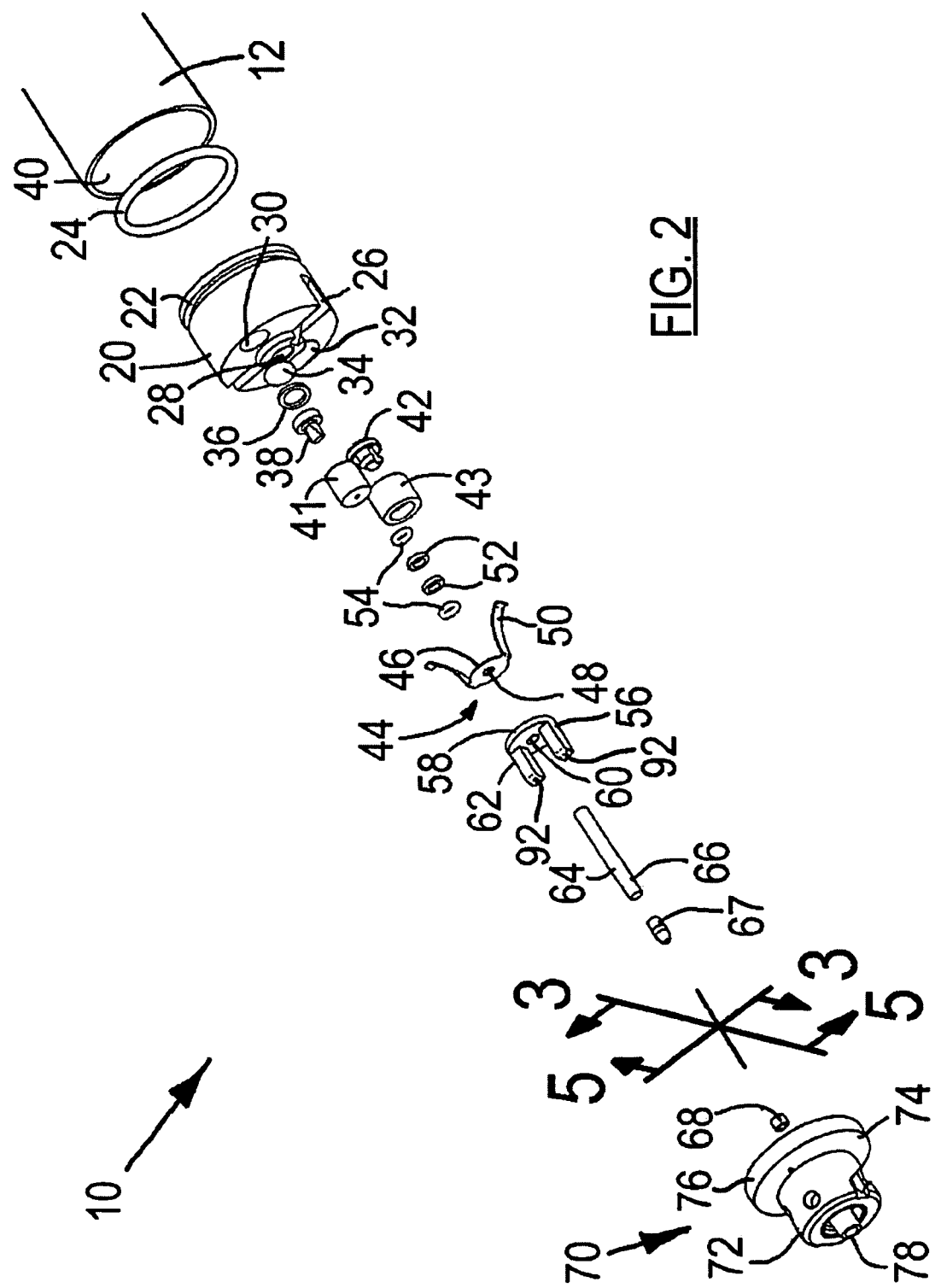
FIG. 2 is a zoomed in view of a portion of FIG. 2.
Figure 3:
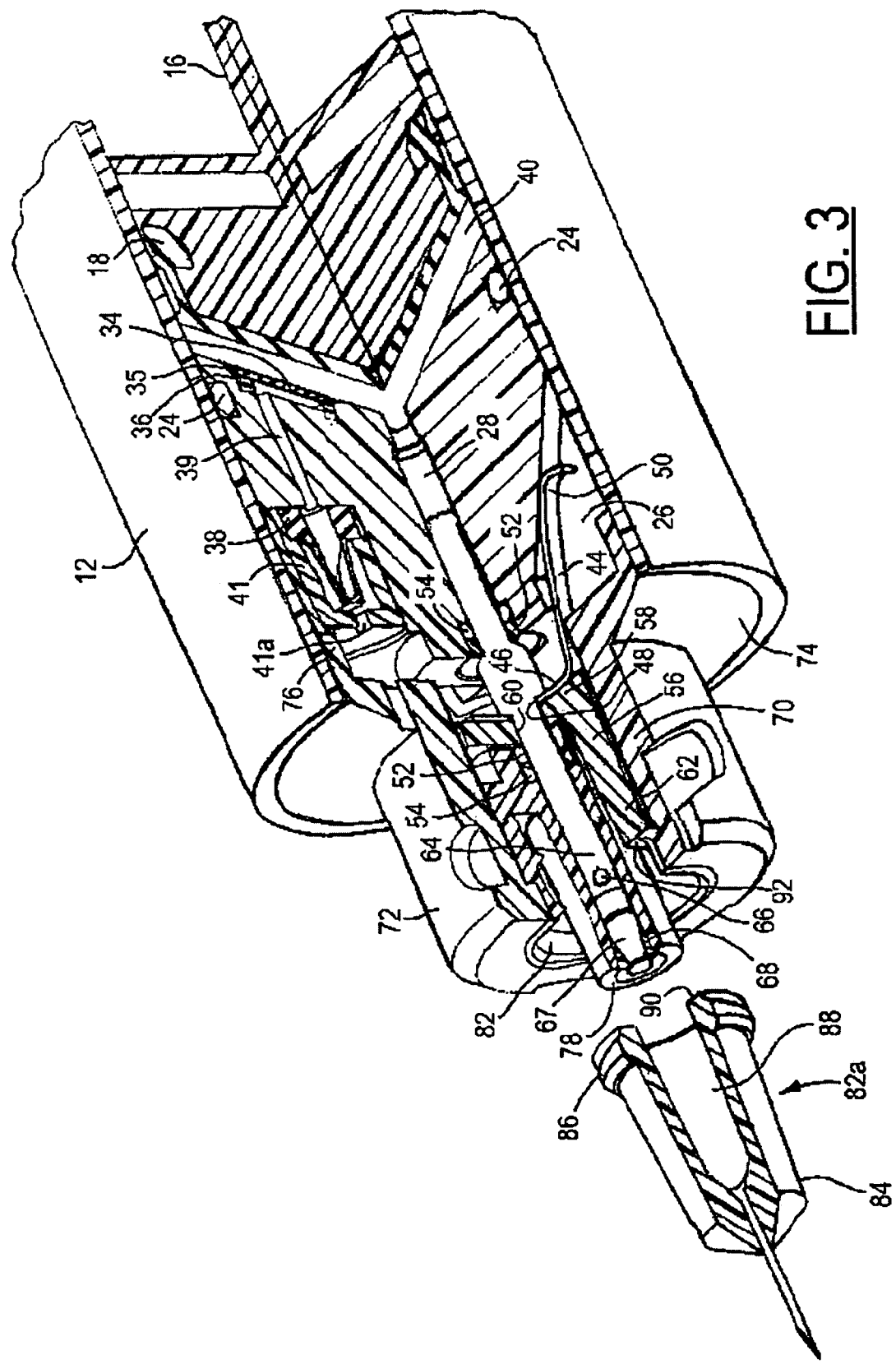
FIG. 3 is a partial cut-away perspective view of a medical dispensing device according to the preferred embodiment of the invention and a needle.
Figure 5:
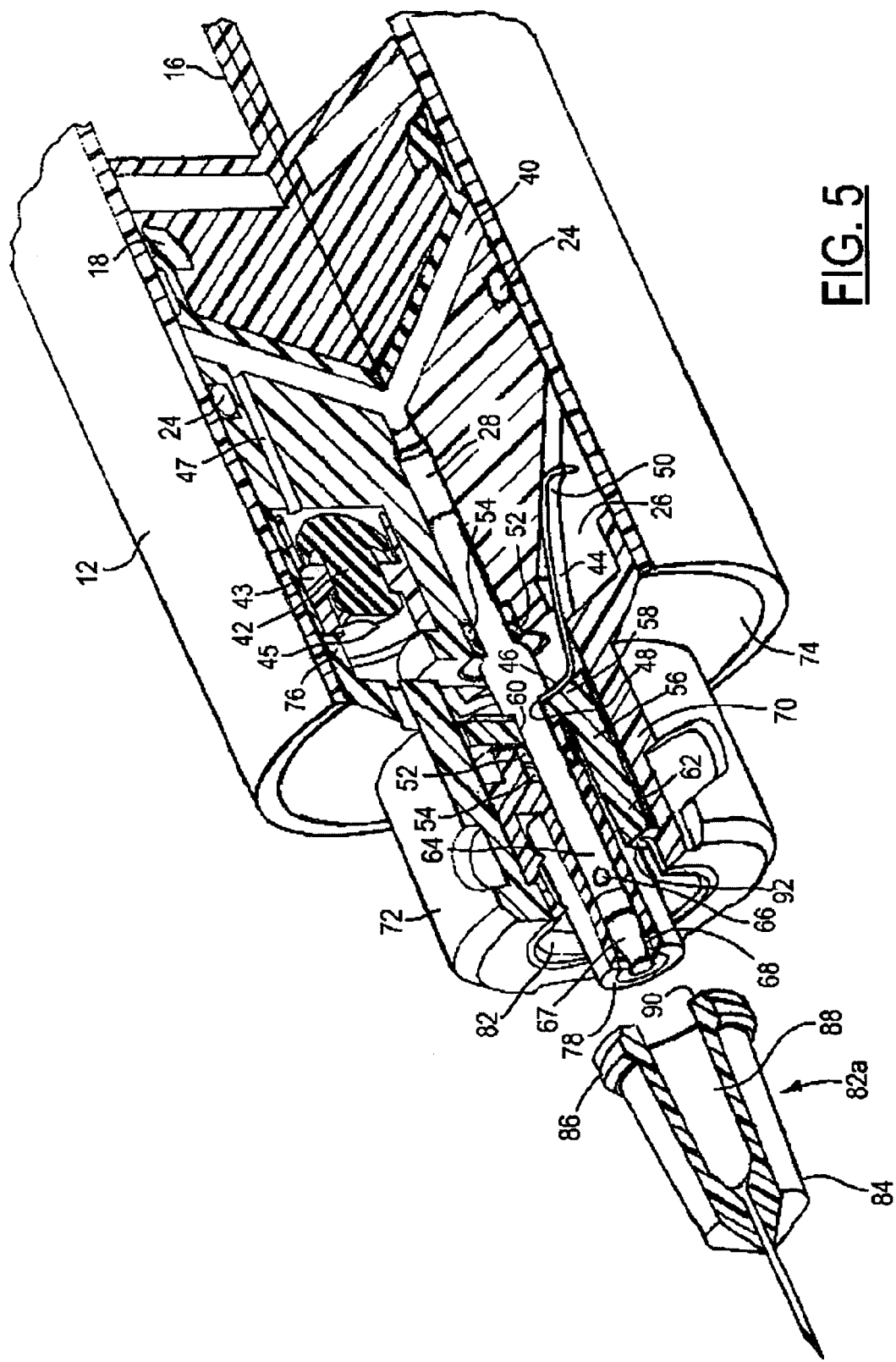
FIG. 5 is a partial cut-away perspective view of the medical dispensing device of FIG. 3 where the device is rotated 180° in a clockwise direction about its central longitudinal axis.

A resilient member 44 having a circular plate 46, central aperture 48 and resilient cam arms 50 is located on the front end of housing 20 (see FIGS. 2, 3, and 5). Cam arms 50 are disposed within slots 26 and can travel radially along the bottom surface of slots 26 as resilient member 44 is moved in a rearward axial direction. In addition, cam arms 50 flex outwardly in response to rearward axial movement of actuating member 56. Central aperture 48 is coaxial with central bore 28. O-rings 52 and O-ring stops 54 are disposed within central bore 28 and adjacent resilient member 44 to provide fluid-tight fit.

An actuating member 56 includes a circular bottom plate 58, a central opening 60, and upstanding arms 62 is located against resilient member 44, with central opening 60 being coaxial with central aperture 48 on resilient member 44 and central bore 28 in housing 20. A valve stem 64 is located within central bore 28, central aperture 48, and central opening 60 for fluid communication with cavity 40 and is attached to actuating member 56 for movement with actuating member 56. Valve stem 64 has openings 66 to permit fluid to enter into the interior of valve stem 64 and eventually to cavity 40. A valve head 67 is attached at the end of valve stem 64 and has a complementary fit to a valve seat 68 for sealing engagement. Collectively, valve assembly 65 comprises valve stem 64 and attached valve head 66. Resilient member 44 abutting against actuating member 56 biases valve head 67 to be seated against valve seat 68 for fluid-tight fit (see FIGS. 3 and 5).

Figure 4:
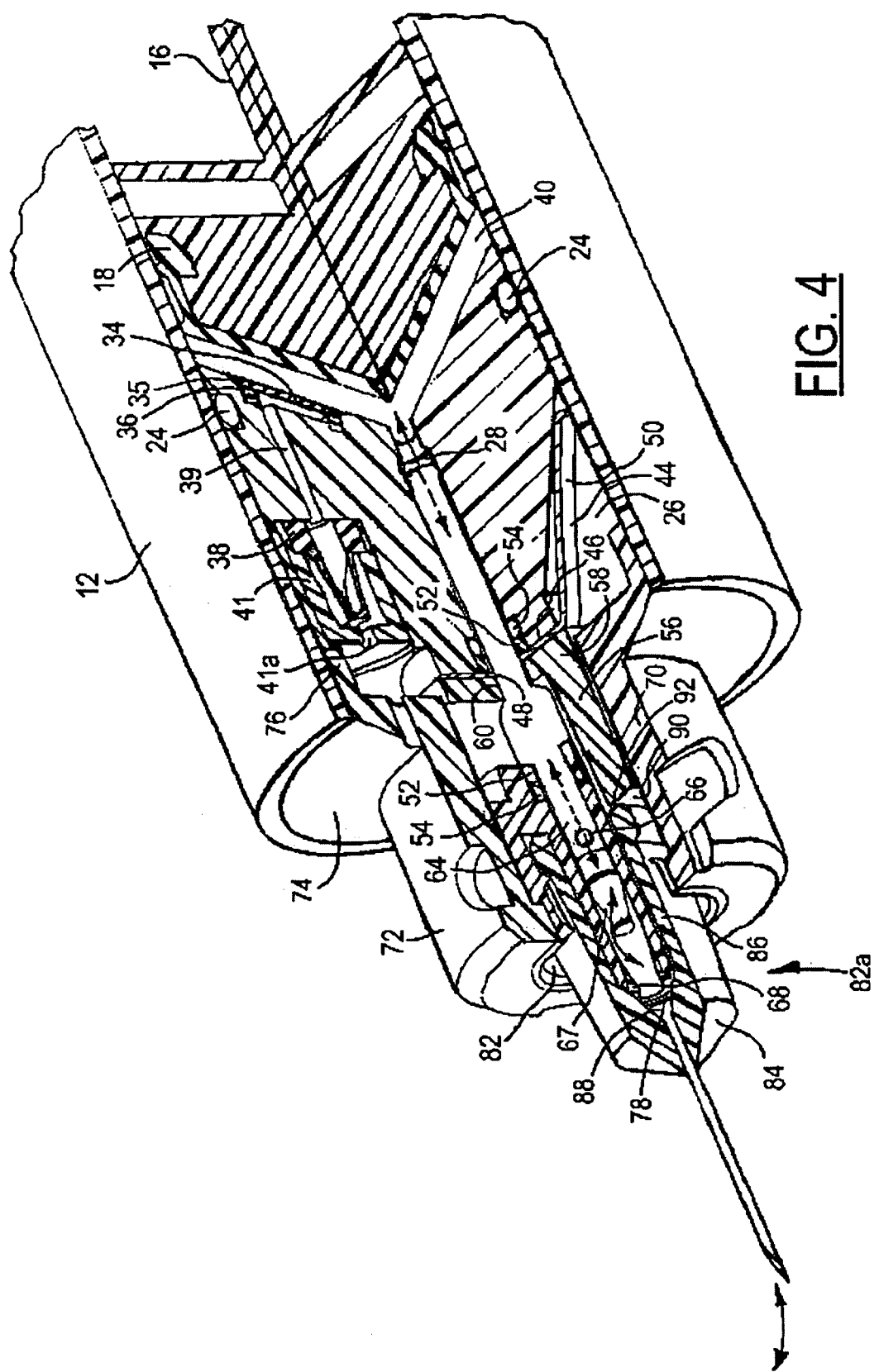
FIG. 4 is a cut-away perspective view of FIG. 3 where a needle is mounted on the end of the medical dispensing device according to the preferred embodiment of the invention.

An end housing 70 comprises a circular side wall 72, a circumferentially and axially extending flange 74, a downwardly extending circumferential lip 76 (as seen in FIGS. 3 to 5), and a tubular housing 78 whose end extends past the end surface of circular side wall 72. Valve seat 68 abuts against the end of tubular housing 78. O-ring 52 and O-ring stop 54 are disposed at the end of tubular housing 78 to provide fluid-tight fit. The inner surface of circular side wall 72 has a male luer portion 82 dimensioned for complementary fit with a female luer portion. As seen in FIGS. 3 and 5, a needle is provided at 82a having a needle housing 84, a female luer portion 86, and a hollow interior 88 dimensioned for complementary fit with tubular housing 78.

As seen in FIG. 4, when needle 82a is attached to end housing 70 by means of male luer portion 82 and female luer portion 86, the bottom surface 90 of needle housing 84 contacts the top surface 92 of actuating member 56 such that rotational movement of needle 82a and the interaction between male luer portion 82 and female luer portion 86 causes actuating member 56 to move in a rearward axial direction. As a result, cam arms 50 flex outwardly and travel downwardly in a radial direction along slots 26. Consequently, valve assembly 65 also moves rearwardly in an axial direction due to valve assembly 65 being attached to actuating member 56, such that there is fluid communication through hollow interior of tubular housing 70. Fluid materials can be then be drawn into cavity 40 under action of plunger 16.

As seen in FIG. 4, hollow interior 88 of needle 82a is co-extensive with the hollow interior of tubular housing 78. Accordingly, there is fluid communication from needle 82a through to cavity 40 by way of fluid flowing (see arrows) through openings 66 in valve stem 64, only when actuating member 56 is engaged by female luer portion 86 and displaced rearwardly and axially sufficient to allow fluid communication through valve assembly 65. When needle 82a is disengaged from end housing 70, resilient cam members 50 flex back to its original position, thus, biasing valve assembly 65 against valve seat 68 for fluid-tight fit.

The scope of the invention also includes a medical dispensing device having any one, or combination, of the following aspects:

a) a valve assembly disposed within an outlet comprising a valve means movable between an open position and a closed position, biasing means for biasing said valve means to a closed position, actuating means disposed within the outlet and coupled to said valve means such that said valve means is movable to an open position when an activating end of a medical accessory is coupled with the outlet;

b) an outlet disposed at an end having a one-way valve for controlling the exchange of gases from the environment to the cavity of the medical dispensing device under the action of a plunger or some other pressurizing means;

c) an outlet disposed at an end having a one-way valve for controlling the exchange of gases from the cavity of the medical dispensing device to the environment under the action of a plunger or some other pressurizing means; and d) an outlet disposed at an end having a two-way valve for controlling the exchange of gases between the cavity of the medical dispensing device to the environment under the action of a plunger or some other pressurizing means.

As will be appreciated, the various aspects of the invention described previously can also be incorporated with the aspects discussed immediately above.

Although the biasing means has been described as a resilient member having been described as having cam arms and a corresponding number of slots 26, it is to be appreciated that the invention encompasses at least one cam arm and at least one corresponding slot. Other embodiments encompass two, three, four or as many cam arms as may be desired or are necessary along with a corresponding number of slots or cam followers. In a further embodiment of valve stem 64, valve stem 64 has at least one aperture 66.

Although the actuating member has been described as having arms, it is to be appreciated that the invention encompasses at least one arm. Other embodiments can encompass two, three, four, or more arms as may be desired or are necessary.

Other filters or filter arrangements can also be used such as using an oleophobic membrane in place of the hydrophobic membrane whereby the oleophobic membrane is useful in filtering fatty or proteinaceous substances such as those found in blood and will perform the same function of preventing liquid from escaping from the cavity of the medical dispensing device to the environment. Further, the oleophobic membrane can be placed in series, proximal to the cavity of the medical dispensing device, with the hydrophobic membrane and/or filter that prevents entry of bacteria, viruses or other materials that would compromise sterility. In addition, a filter having both oleophobic and filter properties to prevent entry of bacteria, viruses, or other materials which would compromise the sterility, can also be used. As well, the filter and hydrophobic membrane and/or oleophobic membrane can be placed in series or otherwise, with the hydrophobic membrane or oleophobic membrane being proximal to the cavity of the medical dispensing device.

The invention claimed is:

1. A medical dispensing device, comprising:
   a body having a cavity to receive fluid materials;
   a first outlet disposed at an end of said body wherein said first outlet includes a male luer end portion;
   a pressure exerting means for the transferal of liquid from said cavity through said first outlet and the transferal of gases between said cavity and the environment; and
   at least one secondary outlet disposed at said end for controlling the exchange of gases between the environment and said cavity under the action of said pressure exerting means,
   further comprising a valve assembly disposed within said first outlet comprising a valve means movable between an open position and a closed position, biasing means for biasing said valve means to a closed position, actuating means disposed within the male luer end portion of said first outlet and coupled to said valve means such that said valve means is movable to an open position when a female luer end portion of a medical accessory is coupled with said male luer end portion.

2. The medical dispensing device of claim 1, wherein the biasing means comprises at least one resilient cam member and at least one cam follower.

3. The medical dispensing device of claim 2, wherein said cam follower is an inwardly and upwardly extending slot disposed on a cylindrical housing, wherein said cylindrical housing has an axial bore dimensioned for fit with said valve means and fluid communication with said body.

4. The medical dispensing device of claim 3 further including a valve housing disposed within said secondary outlet, and having disposed within said valve housing, a valve selected from a one-way valve for controlling the transfer of gases from said cavity to the environment, a one-way valve for controlling the transfer of gases from the environment to said cavity and a two-way valve for controlling the transfer of gases between said cavity and the environment.

5. The medical dispensing device of claim 4 further including a third outlet disposed at said end for controlling the exchange of gases from the environment to said cavity under the action of said pressure exerting means and optionally further including a valve housing disposed within said third outlet, said valve housing having disposed therein either a one way valve for controlling the transfer of gases from the environment to said cavity or a two way valve for controlling the transfer of gases between said cavity and the environment.

6. The medical dispensing device of claim 5 further including a filter to prevent entry of bacteria or viruses into the cavity, and a hydrophobic or oleophobic membrane to prevent liquid from entering said secondary outlet or said third outlet, disposed in series between at least one of said valves and the cavity, with said hydrophobic or oleophobic membrane being proximal to said cavity.

7. The medical dispensing device of claim 5 further including a membrane having hydrophobic properties or oleophobic properties and additionally filter properties, disposed between at least one of said valves and said cavity.

8. The medical dispensing device of claim 7 further including an oleophobic membrane and a hydrophobic membrane, disposed adjacent to one another, the oleophobic membrane being proximal to said cavity.

9. The medical dispensing device of claim 5 further including at least one membrane selected from an oleophobic membrane, a hydrophobic membrane and a hydrophobic membrane in combination with a oleophobic membrane disposed between said cavity and at least one of said valves, subject to the proviso that if the membrane is a hydrophobic membrane in combination with an oleophobic membrane the oleophobic membrane is disposed proximal to the cavity.

10. The medical dispensing device of any of claims 5 or 6-9 wherein said actuating means comprises at least one arm coaxial with said first outlet and a backing means attached thereto, the backing means having an aperture dimensioned for cooperable movement with said valve means.

11. The medical dispensing device of claim 10 wherein the backing means is a circular disk having an outer diameter slightly less that the inner diameter of said first outlet.

12. The medical dispensing device of claim 11 wherein said pressure exerting means is selected from a plunger slidably and sealingly engaged with the interior of said body and a peristaltic pump.

13. The medical dispensing device of claim 10 wherein said pressure exerting means is selected from a plunger slidably and sealingly engaged with the interior of said body and a peristaltic pump.

14. The medical dispensing device of claim 4 further including a filter to prevent entry of bacteria or viruses into the cavity, and a hydrophobic or oleophobic membrane to prevent liquid from entering said secondary outlet or said third outlet, disposed in series between at least one of said valves and the cavity, with said hydrophobic or oleophobic membrane being proximal to said cavity.

15. The medical dispensing device of claim 4 further including a membrane having hydrophobic properties or oleophobic properties and additionally filter properties, disposed between at least one of said valves and said cavity.

16. The medical dispensing device of claim 15 further including an oleophobic membrane and a hydrophobic membrane, disposed adjacent to one another, the oleophobic membrane being proximal to said cavity.

17. The medical dispensing device of claim 4 further including at least one membrane selected from an oleophobic membrane, a hydrophobic membrane and a hydrophobic membrane in combination with a oleophobic membrane disposed between said cavity and at least one of said valves, subject to the proviso that if the membrane is a hydrophobic membrane in combination with an oleophobic membrane the oleophobic membrane is disposed proximal to the cavity.

18. The medical dispensing device of any of claims 4 or 14-17 wherein said actuating means comprises at least one arm coaxial with said first outlet and a backing means attached thereto, the backing means having an aperture dimensioned for cooperable movement with said valve means.

19. The medical dispensing device of claim 18 wherein the backing means is a circular disk having an outer diameter slightly less that the inner diameter of said first outlet.

20. The medical dispensing device of claim 19 wherein said pressure exerting means is selected from a plunger slidably and sealingly engaged with the interior of said body and a peristaltic pump.

21. The medical dispensing device of claim 18 wherein said pressure exerting means is selected from a plunger slidably and sealingly engaged with the interior of said body and a peristaltic pump.

22. The medical dispensing device of claim 1 wherein said actuating means comprises at least one arm coaxial with said first outlet and a backing means attached thereto, the backing means having an aperture dimensioned for cooperable movement with said valve means.

23. The medical dispensing device of claim 22 wherein the backing means is a circular disk having an outer diameter slightly less that the inner diameter of said first outlet.

24. A medical dispensing device, comprising:
a body having a cavity to receive fluid materials;
a first outlet including a male luer end portion disposed at an end of said body;
a pressure exerting means for the transferal of liquid from said cavity through said first outlet and the transferal of gases between said cavity and the environment;
at least one secondary outlet disposed at said end for controlling the exchange of gases between the environment and said cavity under the action of said pressure exerting means;
a valve assembly disposed within said first outlet comprising a valve means movable between an open position and a closed position, biasing means for biasing said valve means to a closed position, actuating means disposed within the male luer end portion of said first outlet and coupled to said valve means such that said valve means is movable to an open position when a female luer end portion of a medical accessory is coupled with said male luer end portion, wherein the biasing means comprises at least one resilient cam member and at least one cam follower and wherein said cam follower is an inwardly and upwardly extending slot disposed on a cylindrical housing, wherein said cylindrical housing has an axial bore dimensioned for fit with said valve means and fluid communication with said body;
a valve housing disposed within said secondary outlet, and having disposed within said valve housing, a valve selected from a one-way valve for controlling the transfer of gases from said cavity to the environment, a one-way valve for controlling the transfer of gases from the environment to said cavity and a two-way valve for controlling the transfer of gases between said cavity and the environment; and
a third outlet disposed at said end for controlling the exchange of gases from the environment to said cavity under the action of said pressure exerting means and optionally further including a valve housing disposed within said third outlet, said valve housing having disposed therein either a one way valve for controlling the transfer of gases from the environment to said cavity or a two way valve for controlling the transfer of gases between said cavity and the environment.

25. The medical dispensing device of claim 24 further including at least one membrane selected from an oleophobic membrane, a hydrophobic membrane and a hydrophobic membrane in combination with a oleophobic membrane disposed between said cavity and at least one of said valves, subject to the proviso that if the membrane is a hydrophobic membrane in combination with an oleophobic membrane the oleophobic membrane is disposed proximal to the cavity.

26. The medical dispensing device of claim 25 wherein the at least one membrane is integral with at least one valve.

27. The medical dispensing device of claim 26 further including a filter disposed between the end of at least one of said valves distal to said cavity and the environment to prevent entry of sterility-compromising contaminants.

28. The medical dispensing device of claim 26 including a membrane having hydrophobic properties or oleophobic properties and additionally filter properties, disposed between at least one of said valves and said cavity.

29. The medical dispensing device of claim 28 including an oleophobic membrane and a hydrophobic membrane, disposed adjacent to one another, the oleophobic membrane being proximal to said cavity.

30. The medical dispensing device of claim 29 wherein the hydrophobic membrane is integral to the valve.

31. The medical dispensing device of claim 25, 27 or 30 further including a filter to prevent entry of bacteria or viruses into the cavity, and a hydrophobic or oleophobic membrane to prevent liquid from entering said secondary outlet or said third outlet, disposed in series between at least one of said valves and the cavity, with said hydrophobic membrane or oleophobic membrane being proximal to said cavity.

32. The medical dispensing device of claim 31 wherein said actuating means comprises at least one arm coaxial with said first outlet and a backing means attached thereto, the backing means having an aperture dimensioned for cooperable movement with said valve means and wherein the backing means is a circular disk having an outer diameter slightly less that the inner diameter of said first outlet.

33. The medical dispensing device of claim 32 wherein said pressure exerting means is selected from a plunger slidably and sealingly engaged with the interior of said body and a peristaltic pump.

34. The medical dispensing device of claim 25 wherein said actuating means comprises at least one arm coaxial with said first outlet and a backing means attached thereto, the backing means having an aperture dimensioned for cooperable movement with said valve means and wherein the backing means is a circular disk having an outer diameter slightly less that the inner diameter of said first outlet.

35. The medical dispensing device of claim 34 wherein said pressure exerting means is selected from a plunger slidably and sealingly engaged with the interior of said body and a peristaltic pump.

* * * * *